United States Patent
Hu et al.

(10) Patent No.: US 9,599,556 B2
(45) Date of Patent: Mar. 21, 2017

(54) REFERENCE SIGNAL GENERATION FOR LOCK-IN AMPLIFIER IN HIGH SENSITIVITY GAS SENSING SYSTEM

(71) Applicant: NEC Laboratories America, Inc., Princeton, NJ (US)

(72) Inventors: Junqiang Hu, Davis, CA (US); Ting Wang, West Windsor, NJ (US)

(73) Assignee: NEC Corporation (JP)

( * ) Notice: Subject to any disclaimer, the term of this patent is extended or adjusted under 35 U.S.C. 154(b) by 0 days.

(21) Appl. No.: 15/089,987

(22) Filed: Apr. 4, 2016

(65) Prior Publication Data

US 2016/0301367 A1 Oct. 13, 2016

Related U.S. Application Data

(60) Provisional application No. 62/144,607, filed on Apr. 8, 2015.

(51) Int. Cl.
*G01N 21/00* (2006.01)
*G01N 21/39* (2006.01)

(52) U.S. Cl.
CPC ... *G01N 21/39* (2013.01); *G01N 2201/06113* (2013.01); *G01N 2201/12* (2013.01)

(58) Field of Classification Search
CPC ......... G01N 21/39; G01N 2201/06113; G01N 2201/12
USPC ........................................................ 356/437
See application file for complete search history.

(56) References Cited

U.S. PATENT DOCUMENTS

| 5,379,630 A * | 1/1995 | Lacey ................. G01N 27/185 324/105 |
| 6,274,879 B1 * | 8/2001 | Best-Timmann ...... B01D 53/30 250/573 |
| 2009/0086191 A1 * | 4/2009 | Bristol ............... G01N 21/0303 356/73 |

(Continued)

*Primary Examiner* — Sunghee Y Gray
(74) *Attorney, Agent, or Firm* — Joseph Kolodka

(57) ABSTRACT

A gas sensing system includes a signal generator including a wavelength tunable laser, the signal generator providing a first periodic signal and a second periodic signal, wherein the first periodic signal comprises a wavelength scanning signal and the second periodic signal comprises a modulation signal; an optical signal absorption path which is wavelength selective, wherein the generated signal covers at least one of the absorbance band; a signal detector that uses lock-in detection to detect a second harmonic of the second periodic signal after absorption, the signal detector further including a local reference generator, a multiplier, and a low pass filter; a local reference includes a first path (ref1) that outputs sinusoidal signal with frequency equals to that of the second signal in signal generator, and a second path (ref2) that outputs sinusoidal signal of two times ref1 frequency; and a local reference generator having a first phase shifter that is configurable from 0 to $2\pi$ and a second phase shifter that shifts 90-degree, wherein the first phase shifter is for an alignment of ref1 with the modulation signal and the second phase shifter provides 90-degree shifts for ref2 from ref1, wherein the first and second paths (ref1 and ref2) are selected by a switch, wherein the switch uses the first path during initialization and the second path for normal operation.

19 Claims, 2 Drawing Sheets

(56) References Cited

U.S. PATENT DOCUMENTS

2014/0220700 A1\* 8/2014 Alexander ............. G01N 21/59
436/164
2015/0089993 A1\* 4/2015 Bitter ........................ G01J 3/28
73/1.06

\* cited by examiner

REFERENCE SIGNAL GENERATION FOR LOCK-IN AMPLIFIER IN HIGH SENSITIVITY GAS SENSING SYSTEM

This application claims priority to Provisional Application 62/144,607 filed Apr. 8, 2015, the content of which is incorporated by reference.

BACKGROUND

The present invention relates to reference signal generation for lock-in amplifier in high sensitivity gas sensing systems.

High sensitivity optical based gas sensing system detects the absorption of a modulated optical signal after passing it through the gas path. The optical signal is generated from a tunable laser whose wavelength changes according to the amplitude of its driving power. The modulating signal includes a first periodic signal (frequency $f_\alpha=2\pi\alpha$) for wavelength tuning, and a second periodic signal (frequency $f_\theta=2\pi\theta$) for modulation. The first periodic signal is usually a ramp (or a saw-tooth signal) for wavelength tuning; the second periodic signal is mostly a sinusoid that has frequency much higher than the first signal. The detector uses lock-in amplifier to remove most of the noise while amplifies the signal.

A lock-in amplifier requires a local reference signal that has the same frequency and phase as the second periodic modulation signal (i.e., frequency $2\pi\theta$). This signal is usually generated through a phase-locked-loop (PLL). The lock-in amplifier converts the signal to DC and uses a very-narrow-band low-pass filter to filter out noise.

FIG. 1 shows a block diagram of a gas sensing system, which includes a signal generator 120, gas-absorption path 106, and signal detector 122. Signal generator 120 further includes electrical signal generator 102, laser and its driving circuit 104. Laser wavelength changes in accordance with the amplitude of its modulation signal. Electrical signal includes a first periodic signal s1, which serves as the main wavelength scanning signal; a second periodic signal s2 with frequency $2\pi\theta$, which is usually sinusoidal and works as a modulation signal; and a DC signal to set the proper bias current for the laser. Optical path 106 has spectral-selective absorption for the selected wavelength in accordance with the gas of interest. Detector system includes a photo-detector and pre-amplifier 108, an optional band-pass filter with central frequency $4\pi\theta$, reference signal 112, multiplier 114, and a low-pass filter 116. Reference signal 112 has frequency of $4\pi\theta$, to detect the second harmonic of the absorbance. A base band output is generated from low-pass filter 116 and carries gas concentration information.

In a gas sensing system, for higher sensitivity and laser fluctuation tolerance, second order demodulation is used which picks the second harmonic (i.e., 2× frequency which is $4\pi\theta$) of the second modulation signal from the absorbed signal, which is the second derivative of the absorption. For such case the local reference signal needs to be 2× the frequency and 90° phase shifted to the second modulation signal. A simple PLL at the second harmonic, in particular in analog circuit, does not work well since the amplitude of the received signal at the second harmonic frequency varies depends on gas density, and can be approximately zero when the gas density (thus the absorption) is extremely low. This may mean "loss of signal" to the PLL. Further, the demodulated signal at the second harmonic frequency is not DC but the second derivative of the absorption. A simple PLL may not converge well even when the signal is not too small.

In addition, a PLL usually converges slowly. For a detector that receives signals from different paths, these signals are unlikely to be aligned, so each time to switch from one path to another, it takes time for the local reference signal to get locked.

Due to the usage of a first signal for wavelength scanning, and the detection of the second harmonic which results in very small signal, a ultra-low-jitter local reference is needed while a traditional phase-locked-loop (PLL) cannot be used. In addition, for application that a single sensing system (in terms of signal generation and detection) is used for multiple sensing paths, which leads to phase differences of the detected signal, a traditional PLL usually takes time to converge whenever switches from one path to another, which greatly reduces system measuring frequency.

SUMMARY

In one aspect, a gas sensing system includes a signal generator including a wavelength tunable laser, the signal generator providing a first periodic signal and a second periodic signal, wherein the first periodic signal comprises a wavelength scanning signal and the second periodic signal comprises a modulation signal; an optical signal absorption path which is wavelength selective, wherein the generated signal covers at least one of the absorbance band; a signal detector that uses lock-in detection to detect a second harmonic of the second periodic signal after absorption, the signal detector further including a local reference generator, a multiplier, and a low pass filter; a local reference includes a first path (ref1) that outputs sinusoidal signal with frequency equals to that of the second signal in signal generator, and a second path (ref2) that outputs sinusoidal signal of two times ref1 frequency; and a local reference generator having a first phase shifter that is configurable from 0 to $2\pi$ and a second phase shifter that shifts 90-degree, wherein the first phase shifter is for an alignment of ref1 with the modulation signal and the second phase shifter provides 90-degree shifts for ref2 from ref1, wherein the first and second paths (ref1 and ref2) are selected by a switch, wherein the switch uses the first path during initialization and the second path for normal operation.

In another aspect, the system provides a first path to generate a first phase-locked local reference at the second modulation signal (i.e., frequency $2\pi\theta$, phase offset 0); a second path that doubles the first local reference frequency and phase shifts it by 90-degree. The reference signal from the second path is applied to the lock-in amplifier for second harmonic detection.

The first path that generating $2\pi\theta$ local reference uses the same base clock as in the source signal for second modulation signal generation. The first path is a lock-in amplifier that converts the second modulation signal to DC; a decision logic that maximizes the DC value for each sensing path by scanning the phase using a digitally controlled phase shifter. The phase shift of each sensing path is recorded and applied whenever that path is switched to.

Advantages of the system may include one or more of the following. This system provides a reliable method to generate phase-locked frequency to enable second order lock-in amplifier detection, which reduces reference signal jitter, and enables fast switching among different signal paths. The system provides a method to generate the phase-locked local reference signal at the second harmonic of the second modulation signal, and a switching method when changing from one path to another.

DESCRIPTION

Figure 1:
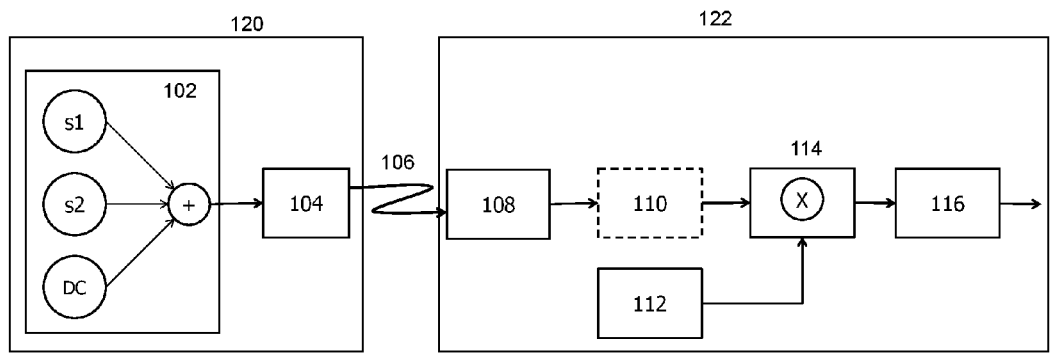
FIG. 1 shows a block diagram of a conventional gas sensing system.
Figure 2:
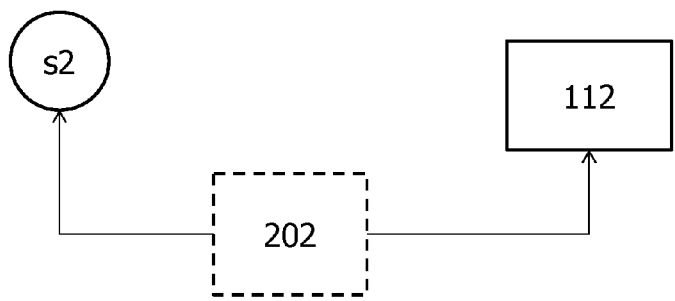
FIG. 2 shows a block diagram of an exemplary gas sensing system.

The present invention uses the same base clock to generate modulation signal s1, and detector local reference, as shown in FIG. 2. The clocks can be from the same clock generator 202, or using separate generator but with same external base input, such as using GPS clock. This guarantees no frequency offset between the two signals.

Figure 3:
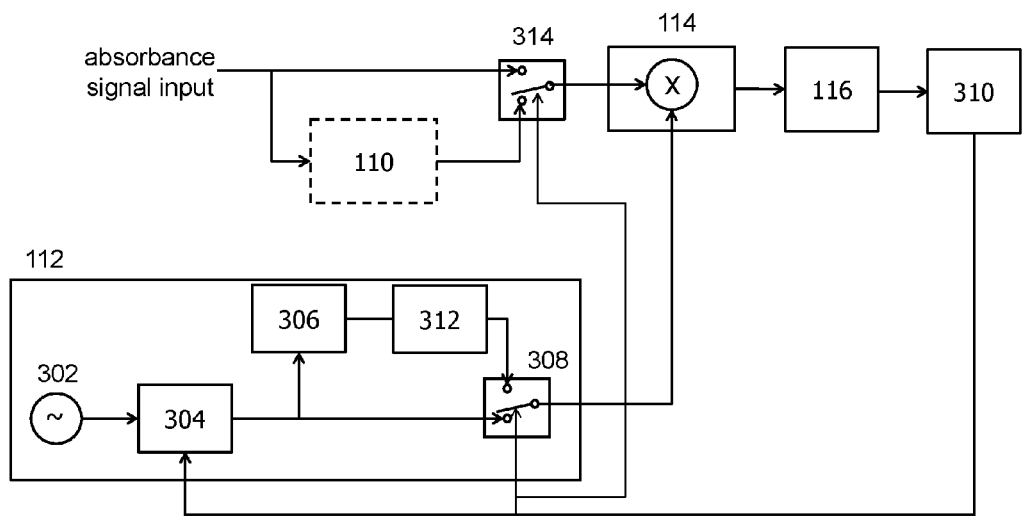
FIG. 3 shows an exemplary local reference generator.

Local reference generator 112 of the preferred embodiment is further shown in FIG. 3. 302 generates a sinusoidal signal with frequency $2\pi\theta$; this signal is fed into a configurable phase shifter 304 for phase correction. The phase shifted signal has one path connected to a switch 308, and another to a frequency doubler 306. Frequency doubler 306 is phase aligned to signal from 304. 312 is a 90-degree phase shifter. Signal from 312 is connected to the second leg of switch 308. Local reference is selected by switch 308 and connected to multiplier 114. Following the signal output from low-pass filter 116, there is a decision and control logic 310 that controls 308 for the selection of local reference, checks the output signal DC level, and configures phase shifter 304.

For signal input, there is one path for first harmonic and a second path for the second harmonic detection. This is achieved by: when local reference is switched to ref1, switch 314 selects from direct input without band-pass filter; when local reference is switched to ref2, switch 314 selects the signal passing through a band-pass filter 110. Note that band-pass filter is optional; selector 314 is not needed when band-pass filter does not exist.

Figure 4:
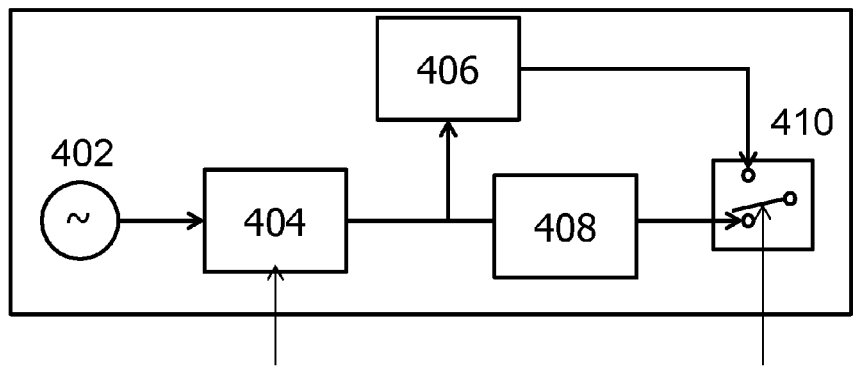
FIG. 4 is an alternative solution to generate the local reference.

FIG. 4 is an alternative solution to generate the local reference. The difference from FIG. 3 is that signal generator 402 outputs sinusoidal signal of $4\pi\theta$(second harmonic frequency of the modulation signal); a frequency divider 406 generates local reference for first harmonic path during initialization/phase-scanning stage. Phase shifter 404, 90-degree phase shifter 408, and reference selector 410 are the same as those in FIG. 3.

System initialization includes phase scanning stage and normal operation stage. When system starts, 301 selects signal from 304 as local reference, then scans with different phase by configuring phase shifter 304. The corresponding phase that generates maximum DC output is considered phase-aligned with input signal and phase shifter 304 is set to that value. Then local reference is switched to the output of 306 and system enters normal operation.

For a system with multiple sensing paths, the above scanning stage is performed for each path. In addition, 310 has a buffer to store the phase shift value of each path with the scanned result. Once the signal path changes, 310 configures 304 with the phase for that path so that the local reference is available immediately.

The system uses two stages of operation to get the optimum phase, and set to that phase for signal detection. The first stage utilizes the first harmonic of the modulation signal, while the second stage which is normal operation stage uses the second harmonic of the absorbance. To enable these two stages, for input signal side, a selector is used to select original input (w/o band-pass filtering) for first harmonic detection, while select the band-passed signal for second harmonic detection. Correspondingly, the local reference generator is able to output signal of $2\pi\theta$ for phase scanning stage and signal of $4\pi\theta$ for normal detection stage.

Figure 5:
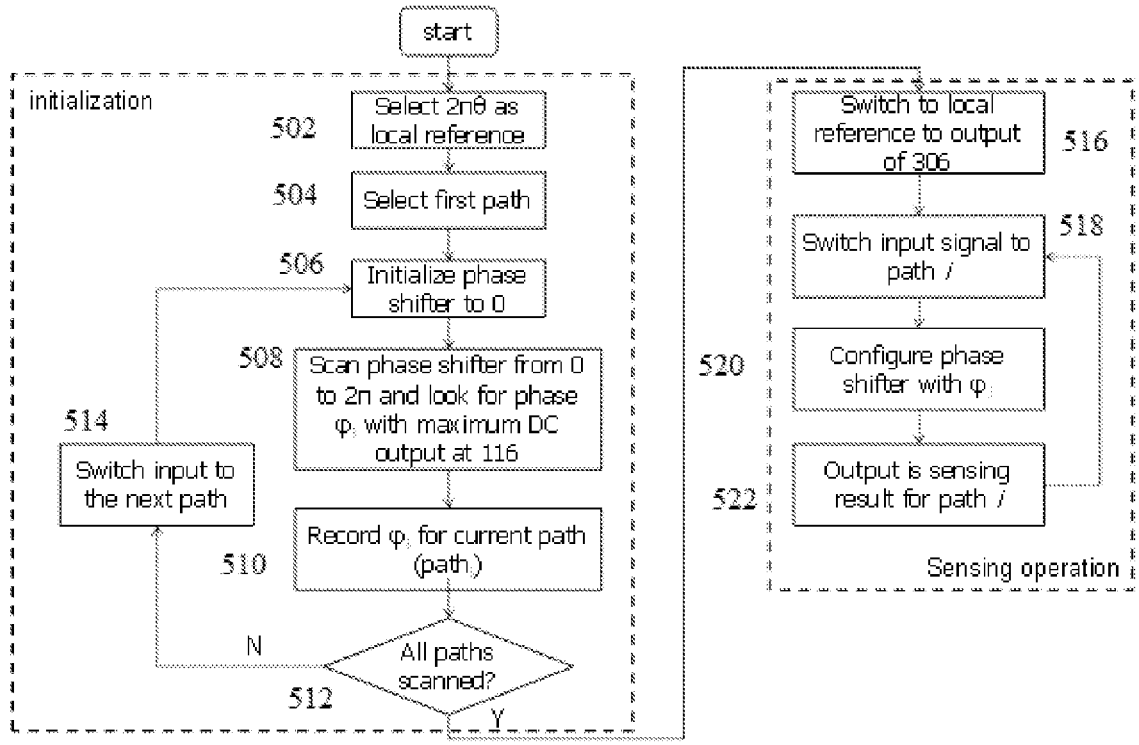
FIG. 5 shows an exemplary process for reference signal generation for lock-in amplifier in high sensitivity gas sensing systems.

FIG. 5 shows an exemplary process for reference signal generation for lock-in amplifier in high sensitivity gas sensing systems. The process includes an initialization mode where it selects a local reference in 502 and then selects a first path in 504. Next, the process initializes the phase shifter to zero in 506. The process scans the phase shifter and looks for a phase with a maximum DC output in 508 and records the phase for the current path in 510. Next, the process checks for to see if all paths have been scanned in 512, and switches the input to next path in 514.

During runtime for sensing operation, the process switches to local reference to the output of block 306 in 516 and switches input signals to path i in 518. The process configures the phase shifter with the phase in 520 and outputs the sensing result for path i in 522.

Embodiments may include a computer program product accessible from a computer-usable or computer-readable medium providing program code for use by or in connection with a computer or any instruction execution system. A computer-usable or computer readable medium may include any apparatus that stores, communicates, propagates, or transports the program for use by or in connection with the instruction execution system, apparatus, or device. The medium can be magnetic, optical, electronic, electromagnetic, infrared, or semiconductor system (or apparatus or device) or a propagation medium. The medium may include a computer-readable storage medium such as a semiconductor or solid state memory, magnetic tape, a removable computer diskette, a random access memory (RAM), a read-only memory (ROM), a rigid magnetic disk and an optical disk, etc.

A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code to reduce the number of times code is retrieved from bulk storage during execution. Input/output or I/O devices (including but not limited to keyboards, displays, pointing devices, etc.) may be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

The foregoing is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that those skilled in the art may implement various modifications without departing from the scope and spirit of the invention. Those skilled in the art could implement various other feature combinations without departing from the scope and spirit of the invention.

What is claimed is:

1. A gas sensing system, comprising
a signal generator including a wavelength tunable laser and a driving circuit, the signal generator providing a first periodic signal and a second periodic signal, wherein the first periodic signal comprises a wavelength scanning signal and the second periodic signal comprises a modulation signal;
an optical signal absorption path wherein the gas being located, said optical signal absorption path being wavelength selective depending on the gas, wherein the generated first periodic signal covers at least one of absorbance band of the gas
a signal detector that uses lock-in detection to detect a second harmonic of the second periodic signal after absorption, the signal detector further including a local reference generator, a multiplier, and a low pass filter;
said local reference generator includes a first path (ref1) that outputs a sinusoidal signal with a frequency equals to the frequency of the second periodic signal in the signal generator, and a second path (ref2) that outputs a sinusoidal signal with a frequency of two times the frequency of the first path (ref1); and said local reference generator having a first phase shifter that is configurable to change a phase ranges from 0 to $2\pi$ and a second phase shifter that shifts a phase 90-degree, wherein the first phase shifter is for an alignment of a beam phase in the first path (ref1) with a phase of the modulation signal and the second phase shifter provides a 90-degree beam phase shifts for the second path (ref2) from the beam phase for the first path (ref1), wherein the first and second paths (ref1 and ref2) are selected by a switch, wherein the switch uses the first path during initialization and the second path for a measurement of the gas.

2. The system of claim 1, comprising a decision and configuration logic in the detector connected to the output of a lock-in amplifier to configure the first phase shifter for optimum detection output.

3. The system of claim 2, wherein the decision and configuration logic uses ref1 as a local reference and configures the first phase shifter from 0 to $2\pi$ and looks for a phase that generates maximum DC at lock-in amplifier output.

4. The system of claim 2, wherein the decision and configuration logic configures the first phase shifter with a phase that generates maximum DC output at lock-in amplifier output, and selects ref2 for absorbance detection.

5. The system of claim 1, wherein the detector has a multiplexer for signal input, wherein the first path takes a direct input signal, and the second path takes a $4\pi\theta$ band-passed signal.

6. The system of claim 5, wherein the detector selects direct input when local reference is ref1; selects band-passed input when local reference is ref2.

7. The system of claim 1, wherein the local reference generator includes a signal generator that outputs sinusoid wave of frequency $2\pi\theta$, followed by configurable phase shifter to generate local reference ref1.

8. The system of claim 7, wherein ref1 is connected to a frequency doubler followed by a 90-degree phase shifter to generate ref2.

9. The system of claim 8, wherein the frequency doubler output is phase-aligned with ref1.

10. The system of claim 1, wherein a local reference generator includes a signal generator that outputs sinusoid wave of frequency $4\pi\theta$, followed by a configurable phase shifter and a frequency divider to generate local reference ref1.

11. The system of claim 10, wherein the configurable phase shifter output is connected to 90-degree phase shifter to generate ref2.

12. The system of claim 10, wherein the frequency divider is phase-aligned with its input.

13. The system of claim 1, wherein the second periodic signal at the generator, and the local reference signal at the detector, are both generated from one base clock source.

14. The system of claim 1, comprising multiple gas paths.

15. The system of claim 14, wherein a length of each path is independent.

16. The system of claim 14, comprising a decision and configuration logic in the detector.

17. The system of claim 16, wherein the decision and configuration logic scans for an optimum phase for each gas path using ref1 as local reference.

18. The system of claim 17, wherein the decision and configuration logic uses ref2 as a local reference, and configures the configurable phase shifter with a optimum shift value for the path under detection.

19. The system of claim 14, comprising a multiplexer at a detector input to select signals.

* * * * *